(12) United States Patent
Bossenmaier et al.

(10) Patent No.: US 7,247,649 B2
(45) Date of Patent: Jul. 24, 2007

(54) OXAZOLES, THEIR MANUFACTURE AND USE AS PHARMACEUTICAL AGENTS

(75) Inventors: Birgit Bossenmaier, Seefeld (DE); Walter-Gunar Friebe, Mannheim (DE); Ulrike Reiff, Penzberg (DE); Matthias Rueth, Penzberg (DE); Edgar Voss, Bichl (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 439 days.

(21) Appl. No.: 10/910,765

(22) Filed: Aug. 3, 2004

(65) Prior Publication Data

US 2005/0038091 A1 Feb. 17, 2005

(30) Foreign Application Priority Data

Aug. 13, 2003 (EP) .................................. 03017652
Jan. 30, 2004 (EP) .................................. 04002037

(51) Int. Cl.
*A61K 31/422* (2006.01)
*C07D 263/30* (2006.01)
*C07D 413/12* (2006.01)

(52) U.S. Cl. .................. 514/374; 548/215; 548/235
(58) Field of Classification Search ................ 548/215, 548/235; 514/374
See application file for complete search history.

(56) References Cited

U.S. PATENT DOCUMENTS 6,716,863 B2 * 4/2004 Tasaka et al. ................ 514/374
6,743,924 B2 * 6/2004 Ikemoto et al. ............. 548/255
7,005,526 B2 * 2/2006 Bossenmaier et al. ....... 548/235

FOREIGN PATENT DOCUMENTS

| EP | 1 270 571 | 1/2003 |
| WO | WO 98/03505 | 1/1998 |
| WO | WO 01/77107 | 10/2001 |
| WO | WO 03/059907 | 7/2003 |

\* cited by examiner

*Primary Examiner*—Golam M. M. Shameem
(74) *Attorney, Agent, or Firm*—George W. Johnston; Patricia S. Rocha-Tramaloni; Gene J. Yao

(57) ABSTRACT

The present invention relates to novel oxazoles of formula (I)

formula (I)

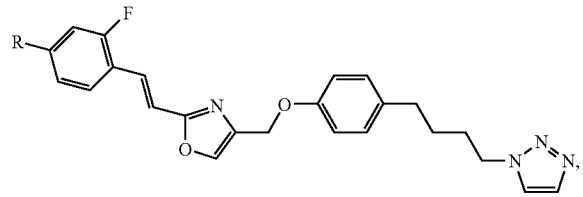

their pharmaceutically acceptable salts, enantiomeric forms, diastereoisomers and racemates, the preparation of the above-mentioned compounds, medicaments containing them and their manufacture, as well as the use of the above-mentioned compounds in the control or prevention of illnesses such as cancer.

5 Claims, No Drawings

OXAZOLES, THEIR MANUFACTURE AND USE AS PHARMACEUTICAL AGENTS

BACKGROUND OF THE INVENTION

The present invention relates to novel oxazole derivatives, to a process for their manufacture, medicaments containing them and their manufacture as well as the use of these compounds as pharmaceutically active agents.

Protein tyrosine kinases (PTKs) catalyse the phosphorylation of tyrosyl residues in various proteins involved in the regulation of cell growth and differentiation (Wilks et al., Progress in Growth Factor Research 97 (1990) 2; Chan, A. C., and Shaw, A. S., Curr. Opin. Immunol. 8 (1996) 394-401). Such PTKs can be divided into receptor tyrosine kinases (e.g. EGFR/HER-1, c-erB2/HER-2, c-met, PDGFr, FGFr) and non-receptor tyrosine kinases (e.g. src, lck). It is known that many oncogenes encode proteins which are aberrant tyrosine kinases capable of causing cell transformation (Yarden, Y., and Ullrich, A., Annu. Rev. Biochem. 57 (1988) 443-478; Larsen et al., Ann. Reports in Med. Chem., 1989, Chpt. 13). Also overexpression of a normal proto-oncogenic tyrosine kinase may result in proliferative disorders.

It is known that receptor tyrosine kinases of the HER-family like HER-2 and EGFR (HER-1) are frequently aberrantly expressed in common human cancers such as breast cancer, gastrointestinal cancer (colon, rectal or stomach cancer), leukemia and ovarian, bronchial and pancreatic cancer. High levels of these receptors correlate with poor prognosis and response to treatment (Wright, C., et al., Br. J. Cancer 65 (1992) 118-121).

Accordingly, it has been recognized that inhibitors of receptor tyrosine kinases are useful as selective inhibitors of the growth of mammalian cancer cells. Therefore several small molecule compounds as well as monoclonal antibodies are in clinical trials for the treatment of various types of cancer (Baselga, J., and Hammond, L. A., Oncology 63 (Suppl. 1) (2002) 6-16; Ranson, M., and Sliwkowski, M. X., Oncology 63 (Suppl. 1) (2002) 17-24).

Some substituted oxazoles are known in the art. WO 98/03505, EP 1 270 571, WO 01/77107 and WO 03/059907 disclose related heterocyclic compounds as tyrosine kinase inhibitors.

It has now surprisingly been found that a specific substitution pattern at the styryl moiety of the present oxazole derivatives leads to an improved activity of the compounds according to the present invention, compared to related compounds known in the art.

SUMMARY

The present invention therefore relates to the new compounds of the general formula (I)

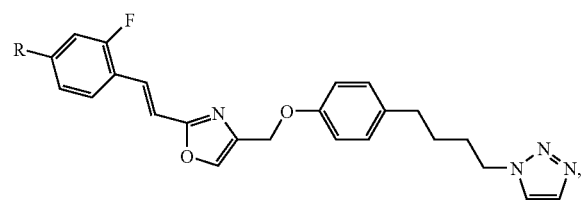

formula (I)

wherein
R is described herewithin below.

The compounds of the present invention show activity as inhibitors of the HER-signalling pathway and therefore possess anti-proliferative activity. Objects of the present invention are the said compounds and their pharmaceutically acceptable salts, the preparation of the above-mentioned compounds, medicaments containing them and their manufacture as well as the use of the above-mentioned compounds in the control or prevention of illnesses, especially of illnesses and disorders as mentioned above or in the manufacture of corresponding medicaments.

DETAILED DESCRIPTION OF THE INVENTION

The present oxazoles are new compounds of the general formula

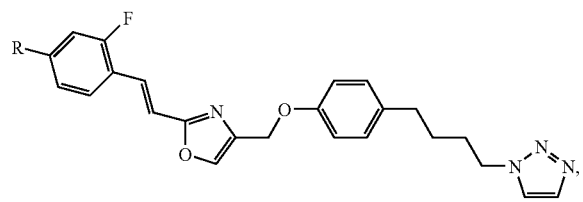

formula (I)

wherein
R is halogen; or a methyl or ethyl group, which optionally may be substituted by one or more halogen atoms
with the proviso that R is not fluoro; and
pharmaceutically acceptable salts thereof.

The term "halogen" as used herein denotes fluorine, chlorine or bromine, preferably fluorine or chlorine.

Preferred substituted methyl or ethyl groups in R are difluoromethyl, trifluoromethyl, or pentafluoroethyl.

It is to be appreciated that the compounds of formula (I) may be present as racemates, enantiomers or as diastereoisomers.

The compounds according to the present invention may exist in the form of their pharmaceutically acceptable salts. The term "pharmaceutically acceptable salt" refers to conventional acid-addition salts that retain the biological effectiveness and properties of the compounds of the present invention and are formed from suitable non-toxic organic or inorganic acids. Sample acid-addition salts include those derived from inorganic acids such as hydrochloric acid, sulfuric acid, sulfamic acid, phosphoric acid and nitric acid and the like, and those derived from organic acids such as p-toluenesulfonic acid, methanesulfonic acid, benzene sulfonic acid and the like. The chemical modification of a pharmaceutical compound (i.e. a drug) into a salt is a technique well known to pharmaceutical chemists to obtain improved physical and chemical stability, hygroscopicity, flowability and solubility of compounds. See, e.g., Ansel, H., et. al., Pharmaceutical Dosage Forms and Drug Delivery Systems, 6th ed., 1995, at pp. 196 and 1456-1457.

A preferred embodiment of the present invention are the compounds of formula (I)
1-[4-(4-{2-[2-(E)-(4-Chloro-2-fluoro-phenyl)-vinyl]-oxazol-4-ylmethoxy}-phenyl)-butyl]-1H-[1,2,3]triazole; and 1-[4-(4-{2-[2-(E)-(2-Fluoro-4-trifluoromethyl-phenyl)-vinyl]-oxazol-4-ylmethoxy}-phenyl)-butyl]-1H-[1,2,3]triazole.

Still another embodiment of the invention is a process for the manufacture of the compounds of formula (I), wherein
(a) the compound of formula (V)

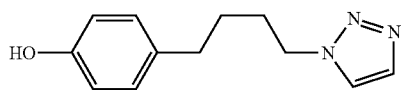

formula (V)

is reacted with a compound of formula (IV)

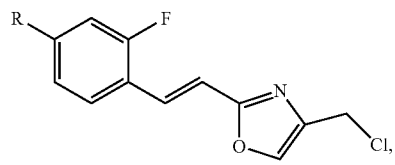

formula (IV)

wherein R has the significance given herein before, to give the respective compound of formula (I);
(b) said compound of formula (I) is isolated from the reaction mixture, and
(c) if desired, converted into a pharmaceutically acceptable salt.

The oxazole derivatives of the general formula (I), or a pharmaceutically acceptable salt thereof, may be prepared by any process known to be applicable for the preparation of chemically-related compounds by the one skilled in the art. Such processes, when used to prepare the oxazole derivatives of formula (I), or a pharmaceutically-acceptable salt thereof, are provided as a further feature of the invention and are illustrated by the following representative examples of scheme 1, in which, unless otherwise stated R has the significance given herein before. Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary skill of an organic chemist.

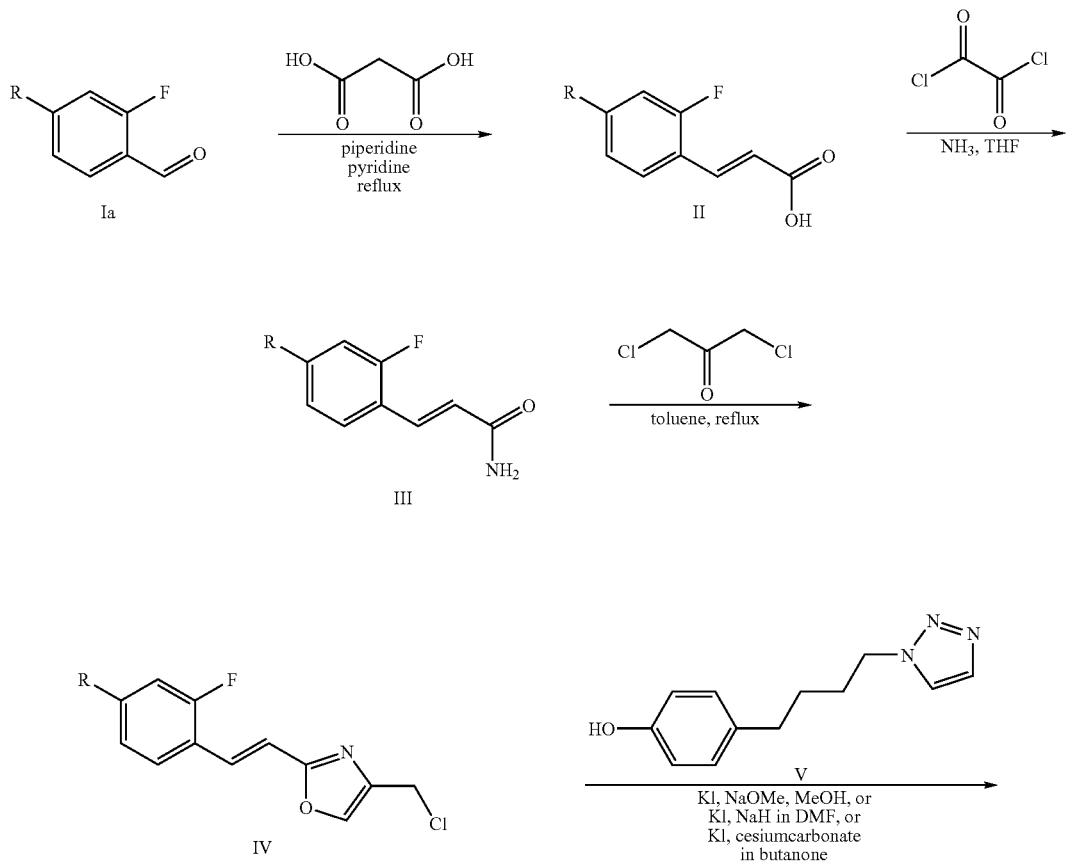

Scheme 1

-continued

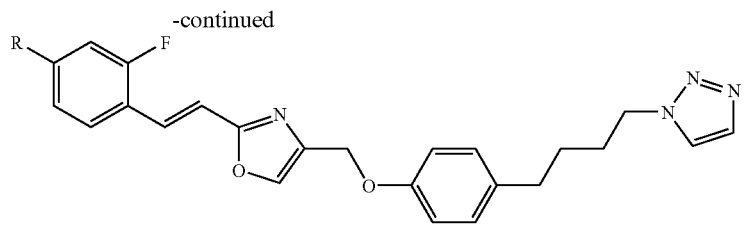

I

A preferred method for the synthesis of the compounds of the present invention starts from the corresponding benzaldehydes (Ia). The first step of the reaction sequence is a Knoevenagel condensation with malonic acid and concomitant decarboxylation, yielding acrylic acids of formula (II). The reaction is typically carried out in solvents like pyridine, N-Methylpyrrolidinone, acetonitrile, N,N-dimethylformamide and mixtures thereof at temperatures up to 140° C. Typically used bases are piperidine, triethylamine and diisopropylamine.

The obtained acrylic acids of formula (II) are converted into their corresponding amides of formula (III) by standard methods for someone skilled in the art, e.g. by activating the carboxylic group in (II) with oxalyl chloride in solvents like tetrahydrofuran, dichloromethane, N,N-dimethylformamide and mixtures thereof at temperatures varying from −30° C. to 40° C. The addition of aqueous ammonia yields said amides of formula (III).

Chlorides of formula (IV) can be synthesized by a commonly known method or a modification thereof. Amides of formula (III) and 1,3-dichloroacetone are subjected to a condensation/dehydration sequence yielding the compounds of formula (IV). Typical solvents for reactions of this kind are toluene, benzene, acetone and chloroform. If desired the reaction can be carried out under solvent free conditions. The reaction temperatures may vary from 50° C. to 150° C.

The oxazole derivatives of formula (I) can be obtained by reactions well known to someone skilled in the art, e.g. by alkylation of 4-(4-[1,2,3]Triazol-1-yl-butyl)-phenol with compounds of formula (IV) according to scheme 1. Typically the alkylation is carried out in the presence of potassium iodide or sodium iodide in solvents like methanol, ethanol, isopropanol, butanone and dimethylformamide. Typical bases for this reaction are sodium methylate, sodium hydride, lithium diisopropyl amide and cesium carbonate. The reaction temperatures may vary from 50° C. to 150° C.

The compounds of the present invention and their pharmaceutically acceptable salts possess valuable pharmacological properties. It has been found that said compounds inhibit the HER-signalling pathway and show anti-proliferative activity. Consequently the compounds of the present invention are useful in the therapy and/or prevention of illnesses with known over-expression of receptor tyrosine kinases of the HER-family like HER-2 and EGFR (HER-1), especially in the therapy and/or prevention of illnesses mentioned above.

According to the present invention a specific substitution pattern and namely the 2-fluoro-substitution at the styryl moiety of the present oxazole derivatives leads to the strong enhancement of activity of the present oxazole derivatives, compared to related compounds known in the art. This is surprising since closely related compounds like the corresponding 3-fluoro-4-chloro- and 3,4-dichloro-compounds, disclosed in examples 1 and 5 herein, do not have reasonable activity. The respective 3-trifluoromethyl compound, disclosed as example 4 herein, is inactive. The respective 4-trifluoromethyl compound, which is 1-[4-(4-{2-[2-(4-trifluoromethyl-phenyl)-vinyl]-oxazol-4-ylmethoxy}-phenyl)-butyl]-1H-[1,2,3]triazole (Example 4, p. 88, WO 01/77107), and is the reference compound in the following biological assay also shows less activity than the compounds of the present invention.

The activity of the present compounds as HER-signalling pathway inhibitors is demonstrated by the following biological asssay:

Assay Description:

A549 cells (human lung carcinoma cell line) were cultivated in RPMI 1640, 2.5% FCS, 2 mM Glutamine, 100 u/ml Penicillin, 100 µg/ml Streptomycin. For the assay the cells were seeded in 384 well plates, 900 cells per well, in the same medium. The next day compounds (dissolved 10 mM in DMSO) were added in various concentrations ranging from 3 µM to 0.15 nM (10 concentrations, 1:3 diluted). After 5 days the MTT assay was done mainly according to the instructions of the manufacturer (Cell proliferation kit I, MTT, from Roche Molecular Biochemicals). In brief: MTT labeling reagent was added to a final concentration of 0.5 mg/ml, added and incubated for 4 hrs at 37 C, 5% CO2. During this incubation time purple formazan crystals are formed. After addition of the solubilization solution (20% SDS in 0.02 M HCl) the plates were incubated overnight at 37° C., 5% CO2. After careful mixing plates were measured in Victor 2 (scanning multiwell spectrophotometer, Wallac) at 550 nm.

A decrease in number of living cells results in a decrease in the total metabolic activity in the sample. The decrease directly correlates to the amount of purple color resulting from the solubilization of the purple formazan crystals.

Cells:

A549: 900 cells in 60 µl per well of 384 well plate (Greiner)

Medium: RPMI 1640, 2.5% FCS, glutamine, pen/strep.

Incubate 1 day at 37° C.

Induction:

Dilution of compound in DMSO: 3 µl 10 mM+27 µl DMSO, dilute 1:3

Add 2 µl of compound dilution row to 95 ul of medium

Add 10 µl of compound dilution to 60 µl medium in test plate→0.3% DMSO per well

Incubate 120 h (5 days) at 37° C., 5% $CO_2$

Analysis:
Add 7 µl MTT (5 mg 7 ml/well), incubate 4 h at 37° C.
Add 30 µl lysis buffer (20% SDS, 0.04 N HCl) per well
Incubate overnight at 37° C.
Measurement:
Victor 2, 550 nm
Determination of $IC_{50}$ was done using XL-fit.
Results:

| Examples | $IC_{50}$ A549 [nM] |
|---|---|
| 1 | 460 |
| 2 | <5 |
| 3 | 2 |
| 4 | 3550 |
| 5 | 900 |
| reference | 7 |

In vivo Assay on Tumor Inhibition:

To generate primary tumors, NSCLC (e.g. QG56, A549, Calu-3) cells (4-5.0×10$^6$ in a volume of 100 µl) are injected subcutaneously into the left flank of female SCID beige or BALB/c nude mice using a 1 ml syringe and a 26 G needle. The tumor cells are originally obtained from the NCI and deposited in a working cell bank. The cells are thawed and expanded in vitro before use in the experiment. Mice are assigned to the treatment groups 14-21 days after cell injection. For grouping (n=10-15 mice per group), the animals are randomized to get a similar mean primary tumor volume of ca. 100-150 mm$^3$ per group. The test compounds are administered orally once per day as a suspension in 7.5% gelatine 0.22% NaCl with an administration volume of 10 ml/kg based on actual body weights. Treatment is initiated one day after staging, and carried out until day 20-50, the final day of the study. The subcutaneous primary tumors are measured twice weekly, starting prior to randomisation, in two dimensions (length and width) using an electronic caliper. The volume of the primary tumor is calculated using the formula: V[mm$^3$]=(length [mm]×width [mm]×width [mm])/2. In addition, the body weight of all animals is recorded at least twice weekly. Finally, at the end of the study the tumors are explanted and weighed.

The compounds according to this invention and their pharmaceutically acceptable salts can be used as medicaments, e.g. in the form of pharmaceutical composition. The pharmaceutical compositions can be administered orally, e.g. in the form of tablets, coated tablets, dragees, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Preferred pharmaceutical compositions comprise the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Microsuspension
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 µm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenise.

The above described preparation yields micro-suspensions of the compounds of the present invention with particle sizes between 1 and 10 µm. The suspensions are suitable for oral applications and can be used in the in vivo assay described above.

Medicaments containing a compound of the present invention or a pharmaceutically acceptable salt thereof and a therapeutically inert carrier are also an object of the present invention, as is a process for their production, which comprises bringing one or more compounds of the present invention and/or pharmaceutically acceptable salts and, if desired, one or more other therapeutically valuable substances into a galenical administration form together with one or more therapeutically inert carriers.

In accordance with the invention the compounds of the present invention as well as their pharmaceutically acceptable salts are useful in the control or prevention of illnesses. Based on their HER-signalling pathway inhibition and their antiproliferative activity, said compounds are useful for the treatment of diseases such as cancer in humans or animals and for the production of corresponding medicaments. The dosage depends on various factors such as manner of administration, species, age and/or individual state of health.

The following examples and references are provided to aid the understanding of the present invention, the true scope of which is set forth in the appended claims. It is understood that modifications can be made in the procedures set forth without departing from the spirit of the invention.

EXAMPLE 1

1-[4-(4-{2-[2-(E)-(4-Chloro-3-fluoro-phenyl)-vinyl]-oxazol-4-ylmethoxy}-phenyl)-butyl]1H-[1,2,3]triazole A mixture of 25.0 g (158 mmol) 4-chloro-3-fluoro-benzaldehyde, 16.4 g (158 mmol) malonic acid, 1.34 g (15.8 mmol) piperidine and 15.0 ml pyridine was kept at reflux temperature until carbon dioxide development ceased (2 h). After cooling to room temperature, the reaction mixture was poured onto 150 g ice and 30 ml 12N HCl. The precipitate was isolated, washed with water and dried. Yield: 26.8 g (85%) 3-(4-chloro-3-fluoro-phenyl)-acrylic acid, melting at 240-245° C.

MS: M=199.2 (API−)

$^1$H-NMR(400 MHz, $D_6$-DMSO): δ=6.64(d, 1H, 2-H), 7.61(m, 2H, Ar—H), 7.63(d, 1H, 3-H), 7.84(dd, 1H, Ar—H), 12.6(br, 1H, COOH).

To a suspension of 20.0 g (100 mmol) 3-(4-chloro-3-fluoro-phenyl)-acrylic acid in 150.0 ml diethyl ether 23.7 g (14.5 ml, 200 mmol) thionyl chloride was added cautiously and the mixture warmed to reflux temperature for 1 h. Stirring was continued over night at room temperature, then the solvents were evaporated. The residue was added to 150 ml of a 25% ice-cold aqueous ammonia solution and stirred for 1 h. The precipitated amide was collected, washed with water and dried at 40° C. in vacuo. Yield: 19.7 g (99%) 3-(4-chloro-3-fluoro-phenyl)-acrylamide.

MS: M=200.2(API+)

$^1$H-NMR(400 MHz, $D_6$-DMSO): δ=6.68(d, 1H, 2-H), 7.20(br, 1H, NH), 7.42(m, 2H), 7.62(m, 3H).

5.0 g (25.0 mmol) 3-(4-chloro-3-fluoro-phenyl)-acrylamide, 3.82 g (30 mmol) 1,3-dichloro acetone and 70.0 ml xylene were kept at reflux temperature for 16 h with continuous removal of water by use of a Dean-Stark trap. After removal of solvents in vacuo, the residue was suspended in 100 ml methanol, heated to reflux temperature and filtered. The filtrate was concentrated and the residue recrystallised from 150 ml methanol/water 1:1, washed with 50 ml cold heptane and dried. Yield: 4.04 g (59%) 4-chloromethyl-2-[2-(4-chloro-3-fluoro-phenyl)-vinyl]-oxazole as tan solid.

MS: M=274.2(API+)

$^1$H-NMR(400 MHz, $D_6$-DMSO): δ=4.71(s, 2H, $CH_2Cl$), 7.29(d, 1H, =CH), 7.53(d, 1H, =CH), 7.61(m, 2H, Ar—H), 7.88(d, 1H, Ar—H), 8.20(s, 1H, oxazole).

A mixture of 0.16 g (0.74 mmol) 4-(4-[1,2,3]triazol-1-yl-butyl)-phenol and 0.14 g cesium carbonate in 20 ml 2-butanone was stirred at 60° C. for 30 min, then 0.20 g (0.74 mmol) 4-chloromethyl-2-[2-(4-chloro-3-fluoro-phenyl)-vinyl]-oxazole and 0.123 g (0.74 mmol) potassium iodide were added and stirring at 60° C. continued over night. After evaporation, 15 ml water was added and the mixture extracted thrice with 15 ml ethyl acetate. The combined organic layers were washed with 1N sodium hydroxide and water, dried over sodium sulfate and evaporated to give 350 mg raw material which was purified on silica gel. Elution with heptane/ethyl acetate 1:1 yielded 167 mg (50%) 1-[4-(4-{2-[2-(E)-(4-chloro-3-fluoro-phenyl)-vinyl]-oxazol-4-yl-methoxy}-phenyl)-butyl]-1H-[1,2,3]triazole as white solid melting at 146-149° C.

MS: M=453.3(API+)

$^1$H-NMR(400 MHz, $D_6$-DMSO): δ=1.48(quintet, 2H), 1.81(quintet, 2H), 2.53(t, 2H), 4.39(t, 2H), 4.98(s, 2H, $CH_2$—O), 6.94(d, 2H, Ar—H), 7.09(d, 2H, Ar—H), 7.29(d, 1H, =CH), 7.52(d, 1H, =CH), 7.63 (m, 2H, Ar—H), 7.71(s, 1H, triazole), 7.88(d, 1H, Ar—H), 8.11(s, 1H, triazole), 8.22(s, 1H, oxazole).

EXAMPLE 2

1-[4-(4-{2-[2-(E)-(4-Chloro-2-fluoro-phenyl)-vinyl]-oxazol-4-ylmethoxy}-phenyl)-butyl]-1H-[1,2,3]triazole To a suspension of 49.0 g (244 mmol) 3-(4-chloro-2-fluoro-phenyl)-acrylic acid in 300 ml tetrahydrofuran and 2.8 ml N,N-dimethylformamide a solution of 26.2 ml (305 mmol) oxalyl chloride in 50 ml tetrahydrofuran was added dropwise at 0° C. within 45 min. Stirring was continued at 0-5° C. for 30 min. and 2 h at room temperature thereafter. The resulting solution was cooled to 0-5° C. again and then added within 15 min. to 750 ml of a 25% aqueous ammonia solution. Tetrahydrofuran was distilled off in vacuo, precipitated amide was collected, washed with water and heptane, then dried at 40° C. in vacuo. Yield: 45.9 g (94%) 3-(4-Chloro-2-fluoro-phenyl)-acrylamide.

$^1$H-NMR(400 MHz, $D_6$-DMSO): δ=6.72(d, 1H, 2-H), 7.23(br, 1H, NH), 7.35(d, 1H, 5'-H), 7.44(d, 1H, 3-H), 7.50(d, 1H, 3'-H), 7.68(br, 1H, NH), 7.95(dd, 1H, 6'-H).

45.0 g (225 mmol) 3-(4-Chloro-2-fluoro-phenyl)-acrylamide, 35.5 g (280 mmol) 1,3-dichloroacetone and 500 ml toluene were kept at reflux temperature for 24 h with continuous removal of water by use of a Dean-Stark trap. After cooling to room temperature, two extractions with 80 ml water, the organic phase was dried over sodium sulphate and the solvent removed in vacuo. The residue was stirred with 80 ml methanol for 30 min., the precipitate filtered, washed with cold methanol, stirred with n-heptane, sucked off and dried in vacuo at 40° C. Yield: 28.9 g (47%) 2-[2-(4-Chloro-2-fluoro-phenyl)-vinyl]-4-chloromethyl-oxazole.

$^1$H-NMR(400 MHz, $D_6$-DMSO): δ=6.72(d, 1H, 1'-H), 7.35(d, 1H, 5"-H), 7.44(d, 1H, 2'-H), 7.50(d, 1H, 3"-H), 7.95(dd, 1H, 6"-H), 8.21(s, 1H, 5-H-oxazole). 26 mg (1.0 mmol) of 95% sodium hydride were given at 0° C. to a solution of 217 mg (1.00 mmol) 4-(4-[1,2,3]triazol-1-ylbutyl)-phenol in 2.0 ml N,N-dimethyl formamide and stirred for 30 min. 272 mg (1.00 mmol) 2-[2-(4-Chloro-2-fluoro-phenyl)-vinyl]-4-chloromethyl-oxazole dissolved in 1.0 ml N,N-dimethyl formamide were added at 0° C., stirring continued at 0° C. for 1 h and 12 h at room temperature thereafter. The mixture was quenched by 6 ml water, stirred for 1 h and the precipitate isolated by filtration. After washing with water, three times with cold ether and drying at 40° C. in vacuo, 350 mg (77%) 1-[4-(4-{2-[2-(E)-(4-chloro-2-fluoro-phenyl)-vinyl]-oxazol-4-ylmethoxy}-phenyl)-butyl]-1H-[1,2,3]triazole were obtained.

MS: M=453.3 (API+).

$^1$H-NMR(400 MHz, D$_6$-DMSO): δ=1.48(quintet, 2H, CH$_2$—CH2-Ph), 1.81(quintet, 2H, CH$_2$—CH2-N), 2.52(t, 2H, CH$_2$-Ph), 4.39(t, 2H, CH$_2$-triazole), 4.98(s, 2H, OCH$_2$-oxazole), 6.94(d, 2H, 3'-,5'-H), 7.09(d, 2H, 2'-,6'-H), 7.25(d, 1H, =CH), 7.36(d, 1H, 5"-H), 7.49-7.55(m, 2H, =CH/3"-H), 7.71(s, 1H, triazole), 7.95(dd, 1H, 6"-H), 8.11(s, 1H, triazole), 8.22(s, 1H, 5-H-oxazole).

EXAMPLE 3

1-[4-(4-{2-[2-(E)-(2-Fluoro-4-trifluoromethyl-phenyl)-vinyl]-oxazol-4-ylmethoxy}-phenyl)-butyl]-1H-[1,2,3]triazole A mixture of 5.0 g (3.55 ml, 26.0 mmol) 2-fluoro-4-trifluoromethyl-benzaldehyde, 3.10 g (29.8 mmol) malonic acid, 0.26 g (0.30 ml, 3.0 mmol) piperidine and 15 ml pyridine was kept at reflux temperature until carbon dioxide development ceased (3 h). After cooling to room temperature the reaction mixture was poured onto 300 g ice and 100 ml 6N HCl. The precipitate was isolated, washed with water, twice with n-heptane and dried. Yield: 5.2 g (85%) 3-(2-Fluoro-4-trifluoromethyl-phenyl)-acrylic acid.

$^1$H-NMR(400 MHz, D$_6$-DMSO): δ=6.73(d, J=16.1 Hz, 1H, 2-H), 7.63(d, 1H, 5'-H), 7.65(d, J=16.1 Hz, 1H, 3-H), 7.76(d, 1H, 3'-H), 8.07(dd, 1H, 6'-H), 12.8(br, 1H, COOH).

To a suspension of 5.00 g (21.4 mmol) 3-(2-fluoro-4-trifluoromethyl-phenyl)-acrylic acid in 30.0 ml tetrahydrofuran and 0.2 ml N,N-dimethyl formamide a solution of 3.60 ml (28.0 mmol) oxalyl chloride in 10 ml tetrahydrofuran was added dropwise at 0° C. within 10 min. Stirring was continued at 0-5° C. for 30 min. and 2 h at room temperature thereafter. The resulting solution was cooled to 0-5° C. again and then added within 15 min. to 150 ml of a 25% aqueous ammonia solution. The separating oily amide was collected and stirred for 30 min. with water. The precipitate was collected, washed with water and dried at 40° C. in vacuo. Yield: 4.4 g (88%) 3-(2-Fluoro-4-trifluoromethyl-phenyl)-acrylamide.

MS: M=234.2 (API+).

$^1$H-NMR(400 MHz, D$_6$-DMSO): δ=6.83(d, 1H, 2-H), 7.31(br, 1H, NH), 7.51(d, 1H, 3-H), 7.63(d, 1H, 5'-H), 7.70(d, 1H, 3'-H), 7.76(br, 1H, NH), 7.89(dd, 1H, 6'-H).

4.00 g (17.1 mmol) 3-(2-Fluoro-4-trifluoromethyl-phenyl)-acrylamide, 2.60 g (21.3 mmol) 1,3-dichloroacetone and 40 ml toluene were kept at reflux temperature for 16 h with continuous removal of water by use of a Dean-Stark trap. After cooling to room temperature, two extractions with 100 ml water, the organic phase was dried over sodium sulphate and the solvent removed in vacuo. Chromatography on silica gel (eluent: n-heptane/ethyl acetate 5:1) gave 1.20 g (23%) 4-chloromethyl-2-[2-(2-fluoro-4-trifluoromethyl-phenyl)-vinyl]-oxazole.

MS: M=306.2 (API+)

$^1$H-NMR(400 MHz, D$_6$-DMSO): δ=4.71(s, 2H, CH$_2$Cl, 7.38(d, J=16.4 Hz, 1H, 1'-H), 7.60(d, J=16.4 Hz, 1H, 2'-H), 7.63(d, 1H, 5"-H), 7.76(d, 1H, 3"-H), 8.14(dd, 1H, 6"-H), 8.23(s, 1H, 5-H-oxazole).

0.305 g (1.00 mmol) 4-Chloromethyl-2-[2-(2-fluoro-4-trifluoromethyl-phenyl)-vinyl]-oxazole, 0.217 g 1.00 mmol) 4-(4-[1,2,3]triazol-1-yl-butyl)-phenol, 0.166 g (1.00 mmol) potassium iodide and 0.191 ml (1.00 mmol) of a 30% sodium methylate solution were added to 50.0 ml methanol and heated to reflux for 10 h. After removal of solvent, partitioning of the residue between 50 ml ethyl acetate and 15 ml water, the organic phase was washed 3× with 15 ml 1 N NaOH, twice with 15 ml water and dried over sodium sulphate. The solution was evaporated to dryness and the residue purified by reversed phase HPLC (C4-column, eluent: methanol/water 8:2+0.2% acetic acid). After evaporation and drying of the product containing fractions, the residue was treated with diethyl ether and dried in vacuo at 40° C. 80 mg (16%) 1-[4-(4-{2-[2-(2-Fluoro-4-trifluoromethyl-phenyl)-vinyl]-oxazol-4-ylmethoxy}-phenyl)-butyl]-1H-[1,2,3]triazole.

MS: M=487.2 (API+).

$^1$H-NMR(400 MHz, D$_6$-DMSO): δ=1.48(quintet, 2H, CH$_2$—CH2-Ph), 1.81(quintet, 2H, CH$_2$—CH2-N), 2.52(t, 2H, CH$_2$-Ph), 4.39(t, 2H, CH$_2$-triazole), 4.99(s, 2H, OCH$_2$-oxazole), 6.94(d, 2H, 3'-,5'-H), 7.09(d, 2H, 2'-,6'-H), 7.39(d, 1H, =CH), 7.59(d, 1H, =CH), 1H, 7.63(d, 1H, 5"-H), 7.71(s, 1H, triazole), 7.77(d, 1H, 3"-H), 8.11(s, 1H, triazole), 8.16(dd, 1H, 6"-H), 8.26(s, 1H, 5-H-oxazole).

EXAMPLE 4

1-[4(4-{2-[2-(E)-(3-Trifluoromethyl-phenyl)-vinyl]-oxazol-4-ylmethoxy}-phenyl)-butyl]-1H-[1,2,3]triazole To a suspension of 5.0 g (22.67 mmol) 3-(3-trifluoromethyl-phenyl)-acrylic acid in 30 ml tetrahydrofuran and 0.3 ml N,N-dimethylformamide a solution of 2.5 ml (29.47 mmol) oxalyl chloride was added dropwise at 0° C. within 45 min. Stirring was continued at 0-5° C. for 30 min. and 2 h at room temperature thereafter. The resulting solution was cooled to 0-5° C. again and then added within 15 min to 20 ml of a 25% aqueous ammonia solution. After stirring for 30 min the organic layer was separated, the aqueous layer extracted with ethyl acetate twice and the combined organic layers dried over Na$_2$SO$_4$. After concentration in vacuo 3-(3-trifluoromethyl-phenyl)-acrylamide was isolated as white solid. Yield 4.83 g(99%).

$^1$H-NMR(400 MHz, D$_6$-DMSO): δ=6.76(d, 1H, 2-H), 7.20(br, 1H, NH), 7.49-7.56 (m, 2H), 7.63-7.74 (m, 2H), 7.87-7.91 (m, 2H) 2.0 g (9.3 mmol) 3-(3-Trifluoromethyl-phenyl)-acrylamide, 4.13 g (32.5 mmol) 1,3-dichloroacetone and 20.0 ml toluene were kept at reflux temperature for 16 h with continuous removal of water by use of a Dean-Stark trap. After removal of solvents in vacuo, the residue was purified by flash column chromatography (heptanes/ethyl acetate 2:1). Yield: 1.92 g (72%) 4-Chloromethyl-2-[2-(3-trifluoromethyl-phenyl)-vinyl]-oxazole as tan solid.

MS: M=288.1(ESI+)

$^1$H-NMR(400 MHz, CDCl$_3$): δ=4.54(s, 2H, CH$_2$Cl), 6.98 (d, 1H, =CH), 7.50-7.71(m, 6H)

26 mg (1.0 mmol) of 95% sodium hydride were given at 0° C. to a solution of 217 mg (1.00 mmol) 4-(4-[1,2,3]triazol-1-yl-butyl)-phenol in 6.0 ml N,N-dimethylformamide and stirred for 30 min. 288 mg (1.00 mmol) 4-Chloromethyl-2-[2-(3-trifluoromethyl-phenyl)-vinyl]-oxazole dissolved in 1.0 ml N,N-dimethylformamide were added at 0° C., stirring continued at 0° C. for 1 h and 12 h at room temperature thereafter. The mixture was quenched by 30 ml water, stirred for 1 h and the precipitate isolated by filtration. After washing with water, three times with cold ether and drying at 40° C. in vacuo, 192 mg (41%) 1-[4-(4-{2-[2-(E)-(3-Trifluoromethyl-phenyl)-vinyl]-oxazol-4-ylmethoxy}-phenyl)-butyl]-1H-[1,2,3]triazole were obtained.

MS: M=469.4 (API+).

$^1$H-NMR(400 MHz, CDCl$_3$): δ=1.62(quintet, 2H, CH$_2$—CH2-Ph), 1.94(quintet, 2H, CH$_2$—$_{CH}$2-N), 2.60(t, 2H, CH$_2$-Ph), 4.39(t, 2H, CH$_2$-triazole), 5.02(s, 2H, OCH$_2$-oxazole), 6.92(d, 2H), 7.0 (d, 1H), 7.07(d, 2H), 7.49-7.60 (m, 4H), 7.69 (m, 3H), 7.76 (s, 1H)

EXAMPLE 5

1-[4-(4-{2-[2-(E)-(3,4-Dichloro-phenyl)-vinyl]-oxazol-4-ylmethoxy}-phenyl)-butyl]-1H-[1,2,3]triazole To a suspension of 5.3 g (23.71 mmol) 3-(3,4-dichloro-phenyl)-acrylic acid in 30 ml tetrahydrofuran and 0.3 ml N,N-dimethylformamide a solution of 3 ml (34.55 mmol) oxalyl chloride was added dropwise at 0° C. within 45 min. Stirring was continued at 0-5° C. for 30 min. and 2 h at room temperature thereafter. The resulting solution was cooled to 0-5° C. again and then added within 15 min to 20 ml of a 25% aqueous ammonia solution. After stirring for 30 min the organic layer was separated, the aqueous layer extracted with ethyl acetate twice and the combined organic layers dried over Na$_2$SO$_4$. After concentration in vacuo and washing with diethyl ether 3-(3,4-dichloro-phenyl)-acrylamide was isolated as white solid. Yield 3.64 g (71%)

$^1$H-NMR(400 MHz, CDCl$_3$): δ=5.66 (br, 2H), 6.44 (d, 1H), 7.32 (d, 1H), 7.45 (d, 1H), 7.55 (d, 1H), 7.60 (s, 1H)

2.3 g (10.6 mmol) 3-(3,4-Dichloro-phenyl)-acrylamide, 4.73 g (37,2 mmol) 1,3-dichloro acetone and 15.0 ml toluene were kept at reflux temperature for 16 h with continuous removal of water by use of a Dean-Stark trap. After removal of solvents in vacuo, the residue was purified by flash column chromatography (heptanes/ethyl acetate 2:1). Yield: 2.88 g (94%) 4-Chloromethyl-2-[2-(3,4-dichloro-phenyl)-vinyl]-oxazole as tan solid.

MS: M=288.1(ESI+)

$^1$H-NMR(400 MHz, CDCl$_3$): δ=4.54(s, 2H, CH$_2$Cl), 6.89 (d, 1H, =CH), 7.33-7.45(m, 3H), 7.59 (s, 1H), 7.62 (s, 1H)

25 mg (1.0 mmol) of 95% sodium hydride were given at 0° C. to a solution of 217 mg (1.00 mmol) 4-(4-[1,2,3]triazol-1-yl-butyl)-phenol in 6.0 ml N,N-dimethylformamide and stirred for 30 min. 288 mg (1.00 mmol) 4-chloromethyl-2-[2-(3,4-dichloro-phenyl)-vinyl]-oxazole dissolved in 1.0 ml N,N-dimethylformamide were added at 0° C., stirring continued at 0° C. for 1 h and 12 h at room temperature thereafter. The mixture was quenched by 30 ml water, stirred for 1 h and the precipitate isolated by filtration. After washing with water, three times with cold ether and drying at 40° C. in vacuo, 225 mg (48%) 1-[4-(4-{2-[2-((E)-3,4-dichloro-phenyl)-vinyl]-oxazol-4-ylmethoxy}-phenyl)-butyl]-1H-[1,2,3]triazole were obtained.

MS: M=470.3 (API+).

$^1$H-NMR(400 MHz, CDCl$_3$): δ=1.62(quintet, 2H, CH$_2$—CH2-Ph), 1.94(quintet, 2H, CH$_2$—CH2-N), 2.60(t, 2H, CH$_2$-Ph), 4.39(t, 2H, CH$_2$-triazole), 5.01(s, 2H, OCH$_2$-oxazole), 6.89-6.93(m, 3H), 7.07(d, 2H), 7.34-7.49(m, 4H), 7.59 (s, 1H), 7.66 (s, 1H), 7.60 (s, 1H)

LIST OF REFERENCES

Ansel, H., et. al., Pharmaceutical Dosage Forms and Drug Delivery Systems, 6th ed., (1995) at pp. 196 and 1456-1457
Baselga, J., and Hammond, L. A., Oncology 63 (2002) 6-16
Chan, A. C., and Shaw, A. S., Curr. Opin. Immunol. 8 (1996) 394-401
EP 1 270 571
Larsen, et al., Ann. Reports in Med. Chem. Chpt. 13 (1989)
Ranson, M., and Sliwkowski, M. X., Oncology 63 (Suppl. 1) (2002) 17-24
Wilks, et al., Progress in Growth Factor Research 97 (1990) 2
WO 01/77107
WO 03/059907
WO 98/03505
Wright, C., et al., Br. J. Cancer 65 (1992) 118-121
Yarden, Y., and Ullrich, A., Annu. Rev. Biochem. 57 (1988) 443-478

What is claimed is:

1. A compound of formula (I)

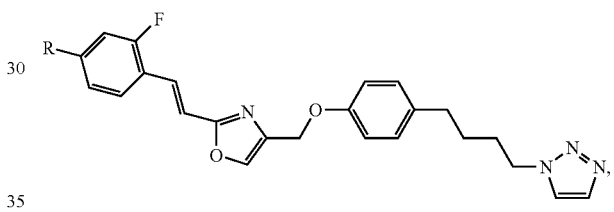

formula (I)

wherein
R is halogen or a methyl or ethyl group, which may optionally be substituted by one or more halogen atoms with the proviso that R is not fluoro; and
pharmaceutically acceptable salts thereof.

2. The compound of claim 1, wherein
R is chloro or trifluoromethyl; and
the pharmaceutically acceptable salts thereof.

3. The compound of claim 1 wherein the compound is 1-[4-(4-{2-[2-(E)-(4-Chloro-2-fluoro-phenyl)-vinyl]-oxazol-4-ylmethoxy}-phenyl)-butyl]-1H-[1,2,3]triazole.

4. The compound of claim 1 wherein the compound is 1-[4-(4-{2-[2-(E)-(2-Fluoro-4-trifluoromethyl-phenyl)-vinyl]-oxazol-4-ylmethoxy}-phenyl)-butyl]-1H-[1,2,3]triazole.

5. A pharmaceutical composition comprising a compound of the formula I

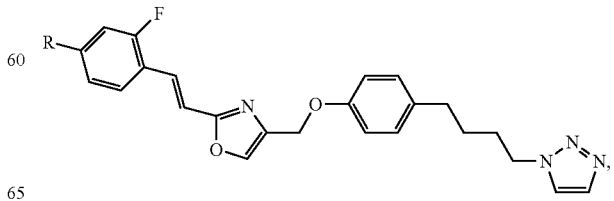

formula (I)

wherein
R is halogen or a methyl or ethyl group which optionally may be substituted by one or more halogen atoms with the proviso that R is not fluoro or a pharmaceutically acceptable salt thereof together with a pharmaceutically acceptable excipient.

* * * * *